United States Patent [19]
McEntire et al.

[11] 4,375,558
[45] Mar. 1, 1983

[54] PURIFICATION OF METHACRYLAMIDOPROPYLTRIMETHYL-AMMONIUM CHLORIDE WITH NONIONIC ORGANIC RESINS

[75] Inventors: Edward E. McEntire; Edward C. Y. Nieh, both of Austin, Tex.

[73] Assignee: Texaco Inc., White Plains, N.Y.

[21] Appl. No.: 309,962

[22] Filed: Oct. 9, 1981

[51] Int. Cl.³ ............................................ C07C 103/44
[52] U.S. Cl. ........................................ 564/206; 564/4
[58] Field of Search ............................. 564/206; 564/4

[56] References Cited

U.S. PATENT DOCUMENTS

| 3,907,891 | 9/1975 | Guilbault | 260/561 N |
| 3,923,741 | 12/1975 | Asano et al. | 564/206 |
| 3,951,600 | 4/1976 | Asano et al. | 564/206 |
| 4,313,001 | 1/1982 | Itoh et al. | 564/206 |

OTHER PUBLICATIONS

Kunin; Robert,"Amber-hi-lites: Porous Polymers as Adsorbents–A Review of Current Practice," Rohm and Haas Technical Bulletin, No. 163, Winter, 1980.
"Summary Bulletin: Amberlite® Polymeric Adsorbents," Rohm and Haas Technical Bulletin, Jun. 1978.
"Amberlite XAD-4, " Rohm and Haas Technical Bulletin, Feb. 1978.
Kunin Amber-hi-lites, Rohm and Haas Bulletin, #161, 1979.
Kunin Chem. Abstracts, vol. 85, #130000, (1976).

Primary Examiner—Arthur P. Demers
Attorney, Agent, or Firm—Jack H. Park; Kenneth R. Priem; David L. Mossman

[57] ABSTRACT

Methacrylamidopropyltrimethylammonium chloride or its free amine, dimethylaminopropylmethacrylamide, is purified by contacting aqueous solutions of the salt or the free amine with solid, nonionic organic resins. Such resins absorb the organic impurities, yet leave behind the polymerization inhibitor.

7 Claims, No Drawings

PURIFICATION OF METHACRYLAMIDOPROPYLTRIMETHYL-AMMONIUM CHLORIDE WITH NONIONIC ORGANIC RESINS

BACKGROUND OF THE INVENTION

1. Field of the Invention

This invention relates to a new process for the purification of methacrylamidopropyltrimethylammonium chloride (MAPTAC) or of the free amine, dimethylaminopropylmethacrylamide (DMAPMA), through the application of adsorption techniques. The invention more particularly relates to the purification, by both batch and continuous processing, of aqueous solutions of MAPTAC or DMAPMA by passing such solutions over a bed of solid, nonionic organic resin or by stirring such solutions with the resin in a batch treatment tank.

2. Description of the Prior Art

Methacrylamidopropyltrimethylammonium chloride, among its other uses, is an important monomer in the synthesis of a class of water soluble cationic polymers which find application as flocculants and as retention aids in the production of paper as taught by U.S. Pat. No. 3,661,880.

Aqueous solutions of commercially available MAPTAC or the free amine vary in color from light yellow to dark amber. This color, or impurity, is carried through upon polymerization of the monomer resulting in polymer products of low molecular weight and widely varying color. Widespread variations in product color or impurities result in polymers having unacceptable performance characteristics. Further, the impurity in the monomer also may cause other undesirable polymer variations such as variations in clarity and viscosity.

While the impurities may be removed effectively from the free amine by vacuum distillation techniques leading to a preferential distillate which is clear and "water white" and which, upon subsequent polymerization, led to a clear and "water white" polymer product, such vacuum distillation techniques do not lend themselves readily to continuous processing and are prohibitively expensive as a commercial process. In addition, the amine is easily activated in this form and may polymerize at distillation temperature, creating additional and undesirable processing problems.

The impurities may also be effectively removed by treatment with activated carbon as described in U.S. Pat. No. 3,907,891. However, as will be shown, the activated carbon treatment will remove the polymerization inhibitor, such as the methylether of hydroquinone (MEHQ), as well as the impurities. Therefore, there remains a need for a method which will remove the impurities from MAPTAC and DMAPMA but which will not appreciably eliminate the presence of any polymerization inhibitor. It is important to have a certain level of polymerization inhibitor in MAPTAC to prevent premature polymerization while the MAPTAC is being stored or shipped.

The method of this invention uses solid, nonionic organic resins as means to remove the organic impurities. One kind of resin, used in the experiments described herein, is the AMBERLITE® XAD series of resins manufactured by Rohm and Haas Company. The Rohm and Haas technical bulletins describe the various uses of the AMBERLITE XAD resins which include water purification, phenol removal, and pesticide and narcotic detection.

SUMMARY OF THE INVENTION

The invention is a process for purifying aqueous solutions of methacrylamidopropyltrimethylammonium chloride or the free amine thereof, dimethylaminopropylmethacrylamide, which comprises contacting an aqueous solution containing from 1 to 99 percent by weight of methacrylamidopropyltrimethylammonium chloride or dimethylaminopropylmethacrylamide with a solid, nonionic organic resin.

DETAILED DESCRIPTION OF THE PREFERRED EMBODIMENT

Impurities which are harmful to the end uses of MAPTAC may be removed by treating the MAPTAC with organic resins. The resins rapidly absorb organic impurities from MAPTAC yet leave behind the polymerization inhibitor, methylether of hydroquinone (MEHQ). Activated charcoal, while absorbing the impurities, will also absorb the MEHQ inhibitor. One of the impurities found in MAPTAC streams is allyl methacrylamide (AMA) which can cause crosslinking in polymers. Color-causing compounds and other impurities which may interfere with subsequent polymerization are also removed by the method of this invention.

Treatment may be conducted by continuously passing the MAPTAC or DMAPMA solution over a bed of organic resin. Stirring the resin with a MAPTAC solution in a batch tank is also effective in removing AMA. Preferably, the treatment level should range from 5 to 35 pounds of monomer per pound of resin.

The solid, nonionic organic resins useful in the method of this invention include polystyrene-divinylbenzene and acrylic resins. Similar resins of crosslinked organic monomers should also be effective. Of particular utility are the AMBERLITE XAD brand of resins. The resin should have a mesh size of from about 20 to 60 mesh. The average particle diameter should be on the order of 0.30 to about 0.45 mm. The resin should be nonionic and hydrophobic.

The resin should also be able to withstand elevated temperatures as the preferred temperature for this purification is from about $-40°$ to $100°$ C. The especially preferred temperature range for the method of this invention is from about $-20°$ to $80°$ C., while the preferred pressure is from ambient to about 500 psi.

It is anticipated that the method of this invention will work for all aqueous solutions of MAPTAC and DMAPMA in all soluble proportions. Generally, this may be expressed as an aqueous solution containing from 1 to 99 percent by weight of MAPTAC or DMAPMA. While the acceptable solvents for MAPTAC and DMAPMA may include any protic solvent, it is preferred that the solvent is water. Other monomers containing quaternary ammonium salts can also be purified by resin treatment. For example, methacrylamidopropylhydroxyethyl dimethyl ammonium acetate (MAPHDA) is a monomer derivative of DMAPMA which may be purified by the resin treatment of this invention. DMAPMA itself may typically be prepared according to the method of U.S. Pat. No. 3,873,247 to Texaco Chemical Co.

The method of this invention is demonstrated in the following examples. Examples I through IV demonstrate a batch processing mode while Example V shows a continuous processing mode.

EXAMPLE I

A MAPTAC sample (50% aqueous) containing 62 ppm AMA and 658 ppm MEHQ inhibitor was stirred magnetically with 3% by weight of AMBERLITE XAD-2 nonionic polymeric adsorbant. After one hour, the MAPTAC sample contained 26 ppm AMA and 556 ppm MEHQ inhibitor. Thus, 58% of the AMA was removed but only 16% of the inhibitor was removed. This characteristic of the resin adsorbent of not removing the same proportion of polymerization inhibitor (i.e., removing less) as proportion of impurity is also seen in the following examples. Indeed, in all examples at least twice as much impurity as polymerization inhibitor is removed, on a percentage basis.

EXAMPLES II-IV

Similar treatments of MAPTAC were conducted with other adsorbents, as shown below. MAPTAC containing 62 ppm AMA and 658 ppm MEHQ was used, and 3 wt.% adsorbent was used.

| Example | Adsorbent | Solution Analysis After 1 Hour | |
|---|---|---|---|
| | | ppm AMA | ppm MEHQ |
| 2 | AMBERLITE XAD-7 | 41 | 544 |
| 3 | AMBERLITE XAD-4 | 21 | 459 |
| 4 | DARCO G-60* | 17 | 100 |

*Powdered activated charcoal from ICI.

Example IV is included for comparison to demonstrate the undesired excess removal of the MEHQ inhibitor by the activated charcoal.

The AMBERLITE resins are macroporous organic resins of moderate surface area available from Rohm and Haas Company. The XAD-2 and XAD-4 resins are made from styrene, and the XAD-7 resin is an acrylic.

EXAMPLE V

This example will show the suitability of this method for use in continuous processing. A 3 cm ID glass column was packed with 90 g (about 130 cc) AMBERLITE XAD-2 resin. MAPTAC solution (50% aq., 62 ppm AMA, 658 ppm MEHQ) was passed over the resin bed at ~0.1 ml per cc of resin per minute, although the rate near the beginning of the experiment was somewhat slower. Each 100 g of MAPTAC effluent was analyzed for AMA and MEHQ. No AMA was detected (detection limit=2 ppm) in the first 700 ml of effluent, and the MEHQ was never less than 100 ppm in any of the first seven fractions. The resin was essentially exhausted after 1600 g of effluent. When a similar experiment was done substituting granulated activated charcoal for the resin, the MEHQ inhibitor was completely removed from the early fractions.

EXAMPLES VI AND VII

To demonstrate the deleterious influence of AMA on the production of high molecular weight polymers, two experiments were performed. Both were identical except that one contained MAPTAC to which 400 ppm AMA had been added.

To a resin kettle equipped with a high speed stirrer, dip tube, addition funnel, and nitrogen pad were charged 256 g of acrylamide (50% aqueous solution) 88.6 g MAPTAC (50% aqueous solution), 44 g deionized water, and 1 ml citric acid solution (2.5% in water). To the addition funnel was charged 162 g n-heptane, 18.4 g SPAN 80 Sorbitan Monooleate, and 1.8 ml initiator solution [17.9% 2,2'-azobis(2,4-dimethylvaleronitrile) in toluene]. Nitrogen was purged through both solutions at 5 and 2.5 l/hr, respectively, for two hours. The nitrogen flow was reduced and the addition funnel contents added rapidly while stirring at 1800 rpm. After 30 minutes of stirring to emulsify, the stir rate was reduced to 1200 rpm, and heating was begun. The temperature was regulated at 50°±2° until the exotherm subsided. Then the reactor contents were heated one hour more at 50° C. Solids were isolated by pouring the emulsion into toluene, then into methanol, and then filtering. Viscosities of 0.1% aqueous solutions of the polymes were 5.6 and 14.1 cp* for the MAPTAC and the MAPTAC+AMA experiments. Thus, even a small amount of AMA can interfere with polymerization and give variable polymer properties.

*Viscosities measured by Nameter vibrating sphere viscometer.

An examination of Examples I through V will show that the nonionic polymer resin effectively removes AMA impurity without removing an appreciable amount of MEHQ inhibitor. The result is in contrast to Example IV where activated charcoal is used. In that example, AMA is removed as in the resin examples, yet the activated charcoal removed much more of the MEHQ inhibitor than did the resin.

Variations and modifications may be made by those skilled in the art without departing from the spirit and scope of the invention which is defined only by the appended claims.

What is claimed is:

1. A process for purifying aqueous solutions of monomers containing quaternary ammonium salts or the free amine thereof without removing the same proportion of a polymerization inhibitor, which comprises contacting an aqueous solution containing from 1 to 99 percent by weight of the monomer in contact with a solid, nonionic organic resin.

2. A process for purifying aqueous solutions of methacrylamidopropyltrimethylammonium chloride or the free amine thereof, dimethylaminopropylmethacrylamide, without removing the same proportion of hydroquinone methylether polymerization inhibitor, which comprises contacting an aqueous solution containing from 1 to 99 percent by weight of methacrylamidopropyltrimethylammonium chloride or dimethylaminopropylmethacrylamide with a solid, nonionic organic resin.

3. The process of claim 1 or 2 in which the treatment level is from 5 to 35 pounds of monomer per pound of resin.

4. The process of claim 1 or 2 in which the resin has a mesh size between 20 and 60 mesh.

5. The process of claim 1 or 2 in which the contacting of the monomer with the resin occurs in a batch processing mode.

6. The process of claim 1 or 2 in which the contacting of the monomer with the resin occurs in a continuous processing mode.

7. The process of claim 1 or 2 in which the contacting of the monomer with the resin occurs at a temperature of about −20° to about 80° C. and a pressure of about ambient to about 500 psi.

* * * * *